(12) United States Patent
Omura

(10) Patent No.: US 6,384,254 B1
(45) Date of Patent: May 7, 2002

(54) QUATERNARY AMMONIUM SALT-CONTAINING POLYSILOXANE, MAKING METHOD, AND FIBER OR FABRIC TREATING AGENT COMPOSITION

(75) Inventor: Naoki Omura, Gunma-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/704,744

(22) Filed: Nov. 3, 2000

(30) Foreign Application Priority Data

Nov. 4, 1999 (JP) .............................. 11-313778

(51) Int. Cl.$^7$ .................................................. C07F 7/10
(52) U.S. Cl. ................................... 556/425; 106/287.11
(58) Field of Search ...................... 556/425; 106/287.11

(56) References Cited

U.S. PATENT DOCUMENTS

| | | | |
|---|---|---|---|
| 3,658,867 A | | 4/1972 | Prokai |
| 3,836,559 A | | 9/1974 | Prokai |
| 4,059,581 A | | 11/1977 | Prokai |
| 4,986,922 A | | 1/1991 | Snow et al. |
| 5,164,522 A | * | 11/1992 | McCarthy et al. ...... 556/425 X |
| 5,235,082 A | | 8/1993 | Hill et al. |
| 5,246,607 A | * | 9/1993 | Schaefer et al. ........ 556/425 X |
| 5,616,758 A | * | 4/1997 | McCarthy et al. ........... 556/425 |
| 6,242,554 B1 | * | 6/2001 | Busch et al. ............ 556/425 X |

FOREIGN PATENT DOCUMENTS

| | | |
|---|---|---|
| JP | 49-11760 | 3/1974 |
| JP | 6-101174 | 4/1994 |
| JP | 6-298775 | 10/1994 |

\* cited by examiner

*Primary Examiner*—Paul F. Shaver
(74) *Attorney, Agent, or Firm*—Birch, Stewart, Kolasch & Birch, LLP

(57) ABSTRACT

A quaternary ammonium salt-containing polysiloxane comprising at least one unit of the formula (1) is formulated into a fiber or fabric treating agent composition which can impart anti-microbial properties, softness and home laundry durability to fibers and fibrous materials.

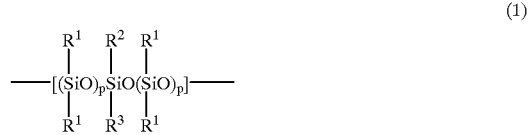

(1)

$R^1$ is a monovalent organic group of 1–20 carbon atoms, $R^2$ is a monovalent organic group containing at least one quaternary ammonium salt, $R^3$ is an organoxy group: —$OR^1$, and p is a positive number of 2 to 2,000.

7 Claims, No Drawings

QUATERNARY AMMONIUM SALT-CONTAINING POLYSILOXANE, MAKING METHOD, AND FIBER OR FABRIC TREATING AGENT COMPOSITION

This invention relates to a quaternary ammonium salt-containing polysiloxane which is useful in formulating a fiber or fabric treating agent composition having anti-microbial properties and imparting softness and home laundry durability to various fibers and fibrous materials, a method for preparing the same, and a fiber or fabric treating agent composition comprising the same.

BACKGROUND OF THE INVENTION

In the prior art, quaternary ammonium salt-containing silanes as typified by 3-(trimethoxysilyl)-propyldimethyloctadecylammonium chloride are widely used as a treating agent for imparting anti-microbial properties to various fibers and fibrous materials. They are less toxic, little stimulative or sensitive to the skin, and home laundry durable on natural fibers such as cotton, but less home laundry durable on synthetic fibers such as polyester and nylon. Since the quaternary ammonium salt-containing silanes are solid, they must be delivered in the form of an alcohol solution, typically methanol solution, which undesirably increases the transportation cost. Since methanol volatilizes upon application, the solution also has a problem of environmental pollution and lacks safety because of the potential risk of ignition.

To eliminate these drawbacks, JP-A 6-101174 proposes a polysiloxane having a quaternary ammonium salt on a side chain and JP-A 6-298775 proposes a compound having a quaternary ammonium salt at either end. These siloxanes are prepared from intermediates, which are expensive since a complex process, is required for their preparation. Additionally, the resulting siloxanes somewhat lack home laundry durability since their adsorption to fibers resorts to only the quaternary ammonium salt group.

SUMMARY OF THE INVENTION

An object of the invention is to provide a novel and improved quaternary ammonium salt-containing polysiloxane which has satisfactory anti-microbial properties and when blended as a main component in a fiber or fabric treating agent composition, imparts softness to various fibers and fibrous materials and maintains the softness even after washing. Another object is to provide a method for preparing the quaternary ammonium salt-containing polysiloxane at a low cost. A further object is to provide a fiber or fabric treating agent composition comprising the quaternary ammonium salt-containing polysiloxane as a main component.

We have found that a novel polysiloxane having a quaternary ammonium salt in the siloxane skeleton is prepared by effecting alcohol-elimination reaction between α,ω-dihydroxydimethylpolysiloxane and a quaternary ammonium salt-containing trialkoxysilane. The starting reactants are relatively easy to prepare and hence, inexpensive. Because of inclusion of both the siloxane skeleton and the alkoxy group, the resulting polysiloxane is highly adsorptive to fibers and highly home laundry durable. Because of the lack of alcohol, the polysiloxane is safe. By using an aminosilane such as an aminopropylaminotrialkoxysilane or N-aminoethyl-3-aminopropyltrialkoxysilane in combination with the reactants, a polysiloxane containing both an amino group and a quaternary ammonium salt-containing group in the skeleton is obtained. The use of the compound has the advantage that softening and anti-microbial treatments can be accomplished at the same time.

It is noted that a siloxane having a quaternary ammonium salt in the siloxane skeleton is disclosed in JP-B49-11760. However, this polymer is used as a foam stabilizer, does not contain an alkoxy group necessary to impart home laundry durability, and does not utilize alcohol-elimination reaction for its synthesis. This polymer is different from the inventive polymer.

Accordingly, the present invention in a first aspect provides a quaternary ammonium salt-containing polysiloxane comprising at least one unit of the following general formula (1):

wherein $R^1$ is a substituted or unsubstituted monovalent organic group of 1 to 20 carbon atoms, $R^2$ is a monovalent organic group containing at least one quaternary ammonium salt, $R^3$ is an organoxy group represented by $-OR^1$, and p is a positive number of 2 to 2,000.

In a second aspect, the invention provides a quaternary ammonium salt-containing polysiloxane comprising at least one terminal group of the following general formula (2):

Wherein R1, R2 and R3 are as defined above, and "a" is equal to 0 or 1.

In a third aspect, the invention provides a method for preparing the quaternary ammonium salt-containing polysiloxane defined above, comprising effecting alcohol-elimination reaction between (A) an organopolysiloxane of the following general formula (5):

wherein $R^1$ and p are as defined above and (B) an organosilane of the following general formula (6):

wherein $R^1$, $R^2$, and $R^3$ are as defined above and "a" is 0 or 1.

Also contemplated herein is a fiber or fabric treating agent composition comprising the quaternary ammonium salt-containing polysiloxane defined above as a main component.

DESCRIPTION OF THE PREFERRED EMBODIMENT

In the present invention, the quaternary ammonium salt-containing polysiloxane is defined as comprising at least one unit of the general formula (1) and/or the general formula (2):

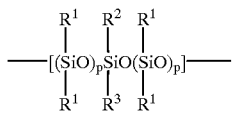
(1)

wherein $R^1$ is a substituted or unsubstituted monovalent organic group of 1 to 20 carbon atoms, $R^2$ is a monovalent organic group containing at least one quaternary ammonium salt, $R^3$ is an organoxy group represented by $-OR^1$, and p is a positive number of 2 to 2,000.

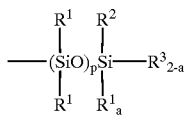
(2)

wherein $R^1$, $R^2$, and $R^3$ are as defined above, and "a" is equal to 0 or 1.

The organic groups represented by $R^1$ are substituted or unsubstituted monovalent organic groups of 1 to 20 carbon atoms, especially 1 to 3 carbon atoms. Illustrative examples of $R^1$ in the organopolysiloxane include alkyl groups such as methyl, ethyl, propyl, butyl, pentyl, hexyl, octyl, decyl, dodecyl, tetradecyl, octadecyl and eicosyl; alkenyl groups such as vinyl, allyl, propenyl, butenyl and hexenyl; aryl groups such as phenyl and tolyl; aralkyl groups such as benzyl, phenylethyl, and phenylpropyl; cycloalkyl groups such as cyclopentyl and cyclohexyl; and substituted ones of the foregoing groups in which some or all of the hydrogen atoms attached to carbon atoms are replaced by halogen atoms, for example, halogenated alkyl groups such as chloromethyl, trifluoropropyl and chlorophenyl, and halogenated aryl groups such as halogenated phenyl. Of these, it is preferred that methyl, phenyl and/or trifluoropropyl account for at least 90 mol % of the $R^1$ groups.

Moreover, in the monovalent hydrocarbon groups (typically alkyl) represented by $R^1$, some of the hydrogen atoms may be replaced by monovalent nitrogenous organic groups such as amino and alkylamino groups. Alternatively, the monovalent hydrocarbon groups represented by $R^1$ may be separated by dibalent nitrogenous organic groups such as NH, NCH$_3$ and NC$_2$H$_5$ groups.

In formula (1), $R^2$ is a monovalent organic group containing at least one quaternary ammonium salt, preferably a monovalent organic group of the following general formula (3):

$$-CH_2CH_2CH_2N^+R^4R^5R^6Cl^-$$ (3)

wherein $R^4$ and $R^5$, which may be the same or different, are each a monovalent hydrocarbon group of 1 to 3 carbon atoms, and $R^6$ is a monovalent hydrocarbon group of 1 to 30 carbon atoms. More preferably, $R^2$ is a monovalent organic group of the following general formula (4):

$$-CH_2CH_2CH_2N^+(CH_3)_2C_nH_{2n+1}Cl^-$$ (4)

wherein n is a positive number of 12 to 24. Examples of the monovalent hydrocarbon groups represented by $R^4$, $R^5$ and $R^6$ are as exemplified above for $R^1$, examples of $R^4$ and $R^5$ being of 1 to 3 carbon atoms and examples of $R^6$ being of 1 to 30 carbon atoms. Most preferably, $R^2$ is $$-CH_2CH_2CH_2N^+(CH_3)_2C_{18}H_{37}Cl^- \text{ or } -CH_2CH_2CH_2N^+(CH_3)_2CH_2C_6H_5Cl^-.$$

$R^3$ is an organoxy group represented by $-OR^1$, preferably an alkoxy group of 1 to 6 carbon atoms. Illustrative examples of $R^3$ are methoxy, ethoxy, and propoxy groups, with the methoxy being most preferred.

Letter p is a positive number of 2 to 2,000. Preferably p is at least 10. Also preferably p is up to 1,000, and especially up to 100. If p is more than 2,000, the content of quaternary ammonium salt becomes relatively low, which detracts from anti-microbial properties.

The quaternary ammonium salt-containing polysiloxane comprising at least one unit of the formula (1) may have any desired terminal group. Exemplary terminal groups are dialkylhydroxysilyl, trialkylsilyl, alkyldialkoxysilyl and dialkylalkoxy groups. Of these, dialkylhydroxysilyl, trialkylsilyl and alkyldialkoxysilyl groups are preferred from the stability standpoint. More preferred terminal groups are of the above general formula (2).

The polysiloxanes of the invention are typically represented by the following general formula (I).

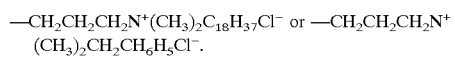
(I)

Herein, $R^1$, $R^2$, $R^3$ and p are as defined above, R' is $-SiR^1{}_2OH$, $-SiR^1{}_2R^3$, $-SiR^1R^3{}_2$ or $-SiR^1{}_aR^2R^3{}_{2-a}$, two R' groups may be the same or different, q is a number of 0 to 30, preferably 1 to 30, and especially equal to 1, 2 or 3 with proviso that the polysiloxane has at least one $R^2$ and at least one $R^3$ in a molecule.

Illustrative examples of the quaternary ammonium salt-containing polysiloxane comprising at least one unit of the formula (1) are given below.

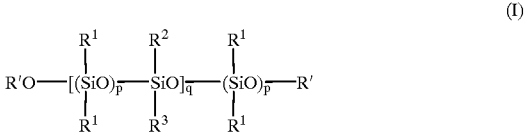

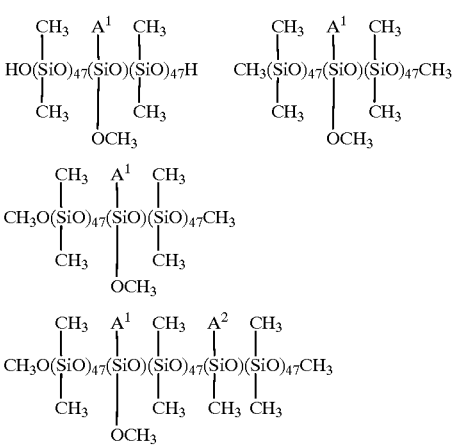

-continued

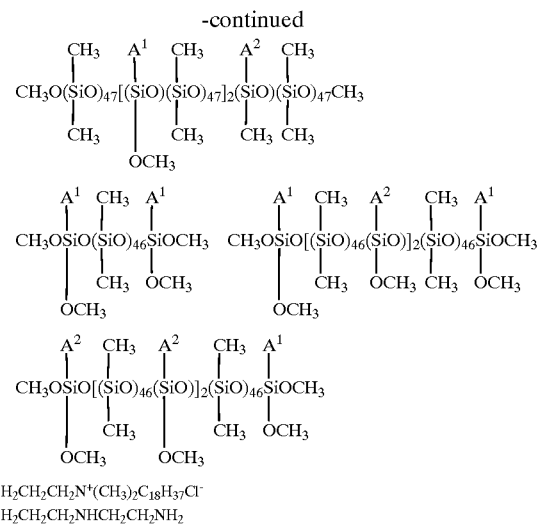

$A^1$: $CH_2CH_2CH_2N^+(CH_3)_2C_{18}H_{37}Cl^-$
$A^2$: $CH_2CH_2CH_2NHCH_2CH_2NH_2$

The quaternary ammonium salt-containing polysiloxane of the invention can be prepared by effecting alcohol-elimination reaction between (A) a both end hydroxyl-blocked Is organopolysiloxane of the following general formula (5) and (B) a quaternary ammonium salt-containing organosilane of the following general formula (6).

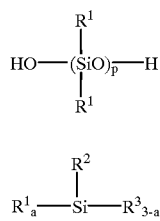
(5)

$R^1_a$—Si—$R^3_{3-a}$ (6)

Herein $R^1$, $R^2$, $R^3$, p and "a" are as defined above.

In formula (5), p is a positive number of 2 to 2,000 as mentioned above. If p is less than 2, the silanol becomes unstable, allowing condensation reaction to take place parallel to the reaction with component (B), resulting in cyclic by-products. $R^1$ is as defined above, and preferably at least 90 mol % of $R^1$ is methyl, phenyl and/or trifluoropropyl. Illustrative examples of the silanol of formula (5) are given below.

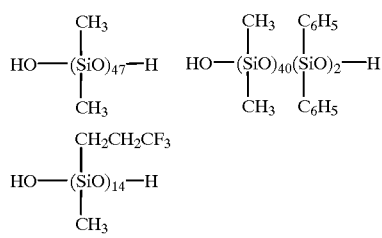

In formula (6), $R^2$ and $R^3$ are as defined in formula (1). It is preferred that $R^2$ be a monovalent organic group of the general formula (3):

—$CH_2CH_2CH_2N^+R^4R^5R^6Cl^-$ (3), and especially —$CH_2CH_2CH_2N^+(CH_3)_2C_{18}H_{37}C^-$ because the corresponding component (B) is effectively reactive with component (A) and ensures ease of synthesis as well as high anti-microbial properties.

$R^3$ is most preferably a methoxy group which allows for smooth progress of alcohol-elimination reaction. Illustrative examples of formula (6) are:

$(CH_3O)_3SiCH_2CH_2CH_2N^+(CH_3)_2C_{18}H_{37}Cl^-$ and $(CH_3O)_3SiCH_2CH_2CH_2N^+(CH_3)_2CH_2C_6H_5Cl^-$.

If desired, an aminosilane is used as component (C) in combination with the silane of formula (6). Examples of the aminosilane are given below.

$(CH_3O)_3SiCH_2CH_2CH_2NH_2$ $(CH_3O)_3SiCH_2CH_2CH_2NHCH_2CH_2NH_2$ $(CH_3O)_3SiCH_2CH_2CH_2NHCH_2CH_2NHCH_2CH_2NH_2$

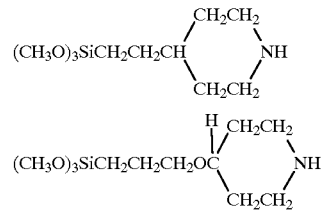

The conditions for reaction between components (A) and (B) preferably include a temperature of about 50 to 180° C. and a time of about 3 to 20 hours although the reaction conditions vary depending on the reactivity of the silanol (A) and the reactivity of the organoxy group, especially alkoxy group in component (B). By effecting reaction under such conditions, the quaternary ammonium salt-containing polysiloxane of formula (1) is readily obtained.

It is noted that since the quaternary ammonium salt as component (B) is generally available in the form of an alcohol solution, typically methanol solution, reaction must be effected in the alcohol solution or the alcohol must be removed prior to reaction. In order that efficient reaction proceed, reaction is preferably effected while removing the alcohol from the system.

As mentioned above, the aminosilane (C) may be used in addition to components (A) and (B) because the aminosilane promotes the alcohol-elimination reaction. The solvent need not be used. If component (A) or the product is viscous, a solvent such as toluene or xylene is conveniently used for the reaction.

Components (A) and (B) are preferably used in such amounts that the: molar ratio of (A)/(B) may range from 0.5/1 to 2.0/1. If (A)/(B) is greater than 2, a more amount of the quaternary ammonium salt-free polysiloxane is left. If (A)/(B) is less than 0.5, a more amount of the quaternary ammonium silane is left.

The thus obtained polysiloxane should preferably contain at least 0.05% by weight of quaternary nitrogen atoms. A quaternary nitrogen atom content of less than 0.05% by weight may fail to exert a satisfactory antimicrobial action.

It is a common practice in the art to modify amino group-containing polysiloxanes by reacting with organic acids, inorganic acids or epoxy compounds. Where the quaternary ammonium salt-containing polysiloxane of the invention is prepared using the aminosilane (C) during reaction between components (A) and (B), the polysiloxane is then optionally modified with organic acids, inorganic acids or epoxy compounds. For example, modification is optionally effected with organic acids, inorganic acids or epoxy compounds in order that one or two hydrogen atoms of NH or $NH_2$ be replaced by COR or $CH_2CH(OH)CH_2O(C_2H_4O)_nR^7$ wherein R is an alkyl group of 1 to 10 carbon atoms, $R^7$ is hydrogen or a monovalent hydrocarbon group, typically an alkyl group of 1 to 8 carbon atoms, and n is a positive number of 0 to 10. Exemplary organic acids are formic acid, acetic acid, acetic anhydride and propanoic acid, with acetic acid and acetic anhydride being preferred. Exemplary inorganic acids are hydrochloric acid and phosphoric acid.

Examples of the epoxy compound which can be used for modification are those of the following general formula (8):

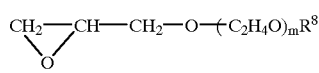

(8)

wherein $R^8$ is hydrogen or a monovalent hydrocarbon group, typically an alkyl group of 1 to 8 carbon atoms, and m is a positive number of 0 to 10. $R^8$ is preferably hydrogen or butyl.

The fiber or fabric treating agent composition comprising the quaternary ammonium salt-containing polysiloxane according to the invention is typically prepared by dissolving the polysiloxane in organic solvents such as toluene, xylene, n-hexane, n-heptane, methyl ethyl ketone, methyl isobutyl ketone, ethyl acetate, butyl acetate, and mineral turpentine; or as emulsions using nonionic, anionic, cationic or ampholytic surfactants. Although the emulsifiers used herein are not critical, exemplary nonionic surfactants include ethoxylated higher alcohols, ethoxylated alkyl phenols, polyhydric alcohol fatty acid esters, ethoxylated polyhydric alcohol fatty acid esters, ethoxylated fatty acids, ethoxylated fatty acid amides, sorbitol, sorbitan fatty acid esters, ethoxylated sorbitan fatty acid esters, and sucrose fatty acid esters, with their HLB being preferably in the range of 5 to 20, especially 10 to 16. Exemplary anionic emulsifiers include higher alcohol sulfate ester salts, alkyl phenyl ether sulfate ester salts, alkylbenzenesulfonate, higher alcohol phosphate ester salts, ethoxylated higher alcohol sulfate ester salts, ethoxylated alkyl phenyl ether sulfate ester salts, and ethoxylated higher alcohol phosphate salts. Exemplary cationic emulsifiers include alkyltrimethylammonium chlorides, alkylamine hydrochlorides, coconut amine acetate, alkylamine acetates, and alkylbenzenedimethylammonium chlorides. Exemplary ampholytic surfactants include N-acylamidopropyl-N,N-dimethylammonium-betaines and N-acylamidopropyl-N,N'-dimethyl-N'-β-hydroxy-propylammoniobetaines. An appropriate amount of the emulsifier or surfactant used is about 5 to 50 parts, more preferably about 10 to 30 parts by weight per 100 parts by weight of the quaternary ammonium salt-containing polysiloxane. Upon emulsification, water is preferably used in such an amount as to give a quaternary ammonium salt-containing polysiloxane concentration of about 10 to 80% by weight, especially about 20 to 60% by weight.

The emulsion may be prepared by prior art well-known methods. For example, the organopolysiloxane is mixed with a surfactant and emulsified in water by means of an emulsifying machine such as a homomixer, homogenizer, colloid mill, line mixer, Universal Mixer®, Ultra Mixer®, Planetary Mixer®, Combi Mix® or three-roll mixer.

In the fiber or fabric treating agent composition, additives may be added insofar as they do not compromise the benefits of the invention. Suitable additives are anti-creasing agents, flame retardants, anti-static agents, anti-oxidants, preservatives, and anti-rusting agents.

A variety of fibers and fibrous materials can be treated with the inventive fiber or fabric treating agent composition, for example, by adjusting the emulsion of the composition to a suitable concentration, and applying the emulsion to fiber or fabrics as by dipping, spraying or roll coating. The amount of the composition applied to fiber or fabrics is not critical and varies with the type of fiber or fabrics. As a general rule, an appropriate coating weight of the quaternary ammonium salt-containing polysiloxane is about 0.01 to 10% by weight based on the weight of fiber or fabrics. The coated fibers are then dried by hot air blowing or in a heating furnace. The drying conditions include about 100 to 150° C. and about 2 to 5 minutes though they vary with the type of fiber or fabrics.

Any desired type of fiber or fibrous material can be treated with the inventive fiber or fabric treating agent composition. The composition is effectively applicable to either natural fibers such as cotton, silk, hemp, wool, Angora and mohair, or synthetic fibers such as polyester, Enylon, acrylic and urethane spandex. Also the form and shape of fiber or fibrous material are not critical. Not only raw material forms such as staples, filaments, tows and threads, but also a variety of worked products including woven fabric, knitted fabric, wadding, and non-woven fabric can be treated with the inventive fiber or fabric treating agent composition.

There has been described a quaternary ammonium salt-containing polysiloxane which is useful in formulating a fiber or fabric treating agent composition for imparting anti-microbial properties, softness and home laundry durability to various fibers and fibrous materials.

EXAMPLE

Examples of the invention are given below by way of illustration and not by way of limitation. In Examples, the viscosity is as measured at 25° C.

Structural analysis by $^{29}$Si-NMR

A 10 mm diameter sample tube was filled with a uniform solution of 1.65 g of a sample, 1.50 g of toluene, 0.20 g of benzene-$d^6$, and 0.04 g of tris(2,4-pentanedionate)chromium as a shiftless relaxation reagent. Using Lambda 300WB (JEOL), peaks of $^{29}$Si-NMR were observed through 600 to 3,000 times of scanning.

Synthesis Example 1

A 1000-ml glass flask equipped with a mechanical agitator blade, condenser and thermometer was charged with 308.3 g (0.100 mol) of α,ω-dihydroxydimethylpolysiloxane of the following average structural formula (9) as component (A) and 261.1 g (0.200 mol) of a 38% solids methanol solution of 3-(trimethoxysilyl)propyldimethyloctadecylammonium chloride as component (B).

(9)

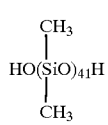

Reaction was effected for 2 hours at 70° C. under methanol reflux. With an ester adapter attached to the flask, the methanol was distilled off in a nitrogen stream. Thereafter, the solution was heated at 120° C. and agitated in a nitrogen stream for 4 hours. After the completion of reaction, there was obtained a highly viscous, colorless, clear oily mass (A-1). This product was identified by $^{29}$Si-NMR structural analysis, with peaks and their attribute shown in Table 1.

TABLE 1

| Chemical shift (ppm) | The number of silicon atoms based on integral ratio | Atrribute |
|---|---|---|
| −22.5 | 42.2 | —SiO— with CH$_3$ groups on Si (CH$_3$/Si/CH$_3$) |
| −43.9 | 0.1 | Unreacted Propyldimethyloctadecylammonium chloride |
| −51.1 | 1.2 | CH$_2$CH$_2$CH$_2$N$^+$(CH$_3$)$_2$C$_{18}$H$_{37}$Cl$^-$ —Si—OCH$_3$ with OCH$_3$ |
| −61.2 | 0.7 | CH$_2$CH$_2$CH$_2$N$^+$(CH$_3$)$_2$C$_{18}$H$_{37}$Cl$^-$ —Si— with OCH$_3$ |

It is understood from the analytical results and reaction route that 95% of 3-(trimethoxysilyl)-propyldimethyloctadecylammonium chloride had reacted with the siloxane polymer and the product contained 60% of a structure of the following average structural formula (10) and 35% of a structure of the following average structural formula (11). The results of measurement of volatile content and rotational viscosity are shown in Table 3.

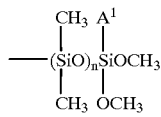

(10)

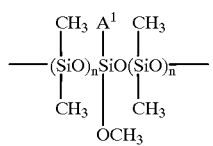

(11)

A$^1$:CH$_2$CH$_2$CH$_2$N$^+$(CH$_3$)$_2$C$_{18}$H$_{37}$Cl$^-$
n = 42

Synthesis Example 2

A 500-ml glass flask equipped with an ester adapter, condenser and thermometer was charged with 308.3 g (0.050 mol) of previously dried α,ω-dihydroxydimethylpolysiloxane of the average structural formula (9) as component (A) and 10.3 g (0.050 mol) of N-β-(aminoethyl)-γ-aminopropylmethyl-dimethoxysilane as component (C). Reaction was effected for 2 hours at 120° C. In the ester adapter, the distillation of methanol resulting from methanol-elimination reaction was lo observed. After cooling, the flask was further charged with 32.7 g (0.025 mol) of a 38% solids methanol solution of 3-(trimethoxysilyl)propyldimethyloctadecylammonium chloride as component (B). Reaction was effected for 4 hours at 70° C. under methanol reflux. The methanol was distilled off in a nitrogen stream. Thereafter, the solution was heated at 120° C. and agitated in a nitrogen stream for 2 hours. After the completion of reaction, there was obtained a viscous, colorless, clear oily mass (A-2). This product was identified by $^{29}$Si-NMR structural analysis, finding that it was represented by the following average structural formula (12).

(12)

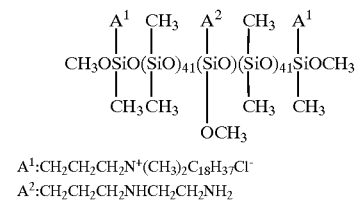

A$^1$:CH$_2$CH$_2$CH$_2$N$^+$(CH$_3$)$_2$C$_{18}$H$_{37}$Cl$^-$
A$^2$:CH$_2$CH$_2$CH$_2$NHCH$_2$CH$_2$NH$_2$

Synthesis Example 3

A 500-ml glass flask equipped with an ester adapter, condenser and thermometer was charged with 308.3 g (0.050 mol) of previously dried α,ω-dihydroxydimethylpolysiloxane of the average structural formula (9) as component (A) and 5.56 g (0.025 mol) of N-β-(aminoethyl)-γ-aminopropylmethyl-trimethoxysilane as component (C). Reaction was effected for 2 hours at 120° C. In the ester adapter, the distillation of methanol resulting from methanol-elimination reaction was observed. After cooling, the flask was further charged with 130.6 g (0.100 mol) of a 38% solids methanol solution of 3-(trimethoxysilyl)propyldimethyloctadecylammonium chloride as component (B). Reaction was effected for 4 hours at 70° C. under methanol reflux. The methanol was distilled off in a nitrogen stream. Thereafter, the solution was heated at 120° C. and agitated in a nitrogen stream for 2 hours. After the completion of reaction, there was obtained a viscous, colorless, clear oily mass (A-3). This product was identified by $^{29}$Si-NMR structural analysis, with peaks and their attribute shown in Table 2.

TABLE 2

| Chemical shift (ppm) | The number of silicon atoms based on integral ratio | Attribute |
|---|---|---|
| −22.5 | 83.2 | —SiO— with CH$_3$ groups |
| −43.9 | 0.3 | unreacted propyldimethyloctadecylammonium chloride |
| −51.2 | 1.2 | CH$_2$CH$_2$CH$_2$N$^+$(CH$_3$)$_2$C$_{18}$H$_{37}$Cl$^-$ —Si—OCH$_3$ with OCH$_3$ |

TABLE 2-continued

| Chemical shift (ppm) | The number of silicon atoms based on integral ratio | Attribute |
|---|---|---|
| −59.1 | 1.0 | CH$_2$CH$_2$CH$_2$NHCH$_2$CH$_2$NH$_2$<br>\|<br>—Si—<br>\|<br>OCH$_3$ |
| −61.2 | 0.5 | CH$_2$CH$_2$CH$_2$N$^+$(CH$_3$)$_2$C$_{18}$H$_{37}$Cl$^-$<br>\|<br>—Si—<br>\|<br>OCH$_3$ |

It is understood from the analytical results and reaction route that 85% of 3-(trimethoxysilyl)-propyldimethyloctadecylammonium chloride had reacted with the siloxane polymer and the product contained 60% of a structure of the average structural formula (10) and 25% of a structure of the average structural formula (11). The results of measurement of volatile content and rotational viscosity are shown in Table 3.

TABLE 3

|  | Synthesis Example 1 | Synthesis Example 2 | Synthesis Example 3 |
|---|---|---|---|
| Polymer | A-1 | A-2 | A-3 |
| Volatile content (%) | 0.5 | 1.0 | 2.0 |
| Rotational viscosity (cp) | 90,000 | 2,450 | 52,000 |
| Amino equivalent (g/mol) | — | 1,700 | 4,100 |

It is noted that the volatile content was measured by heating at 105° C. for 3 hours and that the rotational viscosity was measured by a rotational viscometer.

Examples 1 to 3

To 150 g of the quaternary ammonium salt-containing polysiloxane (A-1), (A-2) or (A-3) obtained in Synthesis Example 1 to 3, was added 90 g of polyoxyethylene tridecyl ether (ethylene oxide added=10 moles, HLB=13.6). After mixing, 160 g of deionized water was added to the mixture, which was agitated for 15 minutes at a high speed by means of a homomixer, achieving phase inversion and thorough milling. Further, 600 g of deionized water was added to the emulsion for dilution, which was agitated for 15 minutes at 2,000 rpm by means of the homomixer, yielding a milky white emulsion.

The emulsion was diluted to an aqueous solution having a silicone solid concentration of 2.0% by weight. A polyester/cotton (65%/35%) mixed broad-cloth was dipped in the solution for one minute, nipped through rolls at a nip rate of 100%, dried at 135° C. for one minute and heat treated at 165° C. for 2 minutes. The thus treated cloth was laundered ten times in accordance with the 103 method of JIS L-0217 whereupon a percentage loss of stephelococcus Aureus was compared by the shaking flask method. The texture of the treated cloth was examined by finger touch before and after washing. The results are shown in Table 4.

For comparison purpose, using a 38% solids methanol solution of 3-(trimethoxysilyl) propyldimethyloctadecylammonium chloride, a 3.5 wt% solids aqueous solution was prepared. A similar experiment was carried out. This is Comparative Example 1. The results are also shown in Table 4.

TABLE 4

|  | E1 | E2 | E3 | CE1 |
|---|---|---|---|---|
| Silicon fluid | A-1 | A-2 | A-3 | — |
| Quaternary ammonium salt content in treating bath (wt %) | 0.10 | 0.03 | 0.05 | 0.10 |
| Bacteria loss after washing (%) | 65 | 80 | 97 | 35 |
| Softness before wash | Somewhat poor | good | good | rough/hard |
| Softness after wash | rough/hard | good | good | rough/hard |

It is evident from the above data that as compared with the prior art silicone-based anti-microbial agent, the fiber or fabric treating agent composition of the invention using the quaternary ammonium salt-containing polysiloxane having home laundry durability and anti-microbial properties has the advantages including the absence of alcohol and the simultaneous accomplishment of fiber treatment and anti-microbial treatment.

Japanese Patent Application No. 11-313778 is incorporated herein by reference.

Reasonable modifications and variations are possible from the foregoing disclosure without departing from either the spirit or scope of the present invention as defined by the claims.

What is claimed is:

1. A quaternary ammonium salt-containing polysiloxane comprising at least one terminal group of the following general formula (2):

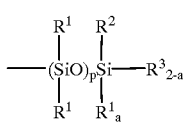

(2)

wherein "a" is equal to 0 or 1 and R$^1$ is a substituted or unsubstituted monovalent organic group of 1 to 20 carbon atoms, R$^2$ is a monovalent organic group containing at least one quaternary ammonium salt, R$^3$ is OR$^1$, and p is a positive number of 2 to 2000.

2. The quaternary ammonium salt-containing polysiloxane of claim 1 wherein R$^2$ is a monovalent organic group of the following general formula (3):

—CH$_2$CH$_2$CH$_2$N$^+$R$^4$R$^5$R$^6$Cl$^-$      (3)

wherein R$^4$ and R$^5$, which may be the same or different, are each a monovalent hydrocarbon group of 1 to 3 carbon atoms, R$^6$ is a monovalent hydrocarbon group of 1 to 30 carbon atoms and R$^2$ is a monovalent organic group of the following general formula (4):

—CH$_2$CH$_2$CH$_2$N$^+$(CH$_3$)$_2$C$_n$H$_{2n+1}$Cl$^-$      (4)

wherein n is a positive number of 12 to 24.

3. A method for preparing a quaternary ammonium salt-containing polysiloxane, comprising effecting alcohol-elimination reaction between (A) an organopolysiloxane of the following general formula (5):

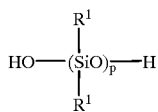
(5)

wherein $R^1$ and p are as defined in claim 2 and (B) an organosilane of the following general formula (6):

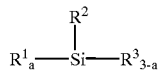
(6)

wherein $R^1$, $R^2$, $R^3$ and "a" are as defined in claim 2.

4. A fiber or fabric treating agent composition comprising the quaternary ammonium salt-containing polysiloxane of claim 1 as a main component.

5. The quaternary ammonium salt-containing polysiloxane of claim 2 which is represented by the following general formula (I):

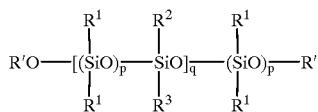
(I)

wherein $R^1$ is $-SiR^1{}_2OH$, $-SiR^1{}_2R^3$, $-SiR^1R^3{}_2$ or $-SiR^1{}_aR^2R^3{}_{2-a}$, two $R^1$ groups may be the same or different, q is a number of 0 to 30 with proviso that the polysiloxane has at least one $R^2$ and at least one $R^3$ in a molecule and at least one $R^1$ is $-SiR^1{}_aR^2R^3{}_{2-a}$.

6. The quaternary ammonium salt-containing polysiloxane of claim 5, wherein q is 1 to 30.

7. The quaternary ammonium salt-containing polysiloxane of claim 1, comprising at least one unit of the following general formula (1):

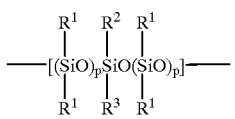
(1)

wherein $R^1$ is a substituted or unsubstituted monovalent organic group of 1 to 20 carbon atoms, $R^2$ is a monovalent organic group containing at least one quaternary ammonium salt, $R^3$ is an organoxy group represented by $-OR^1$, and p is a positive number of 2 to 2000.

* * * * *